United States Patent [19]

Iskra

[11] Patent Number: 5,021,050
[45] Date of Patent: Jun. 4, 1991

[54] ABSORBENT PANEL STRUCTURE
[75] Inventor: Michael J. Iskra, Kent, Wash.
[73] Assignee: Weyerhaeuser Company, Federal Way, Wash.
[21] Appl. No.: 448,710
[22] Filed: Dec. 11, 1989
[51] Int. Cl.⁵ .............................................. A61F 13/00
[52] U.S. Cl. ...................................... 604/379; 604/368
[58] Field of Search ............... 604/368, 379, 374, 367, 604/375

[56] References Cited

U.S. PATENT DOCUMENTS

| 3,017,304 | 1/1962 | Burgeni | 604/375 |
|---|---|---|---|
| 3,670,731 | 6/1972 | Harmon | 604/368 |
| 3,860,003 | 1/1975 | Buell | 604/385.2 |
| 3,938,522 | 2/1976 | Repke | 604/365 |
| 4,102,340 | 7/1978 | Mesek et al. | 604/368 |
| 4,103,062 | 7/1978 | Aberson et al. | 428/283 |
| 4,186,165 | 1/1980 | Aberson et al. | 264/112 |
| 4,235,237 | 11/1980 | Mesek et al. | 604/368 |
| 4,340,057 | 7/1982 | Bloch et al. | 604/358 |
| 4,364,992 | 12/1982 | Itoh et al. | 428/283 |
| 4,500,315 | 2/1985 | Pieniak et al. | 604/379 |
| 4,537,590 | 8/1985 | Pieniak et al. | 604/379 |
| 4,540,454 | 9/1985 | Pieniak et al. | 156/62.2 |
| 4,559,050 | 12/1985 | Iskra | 604/368 |
| 4,573,988 | 3/1986 | Pieniak et al. | 604/368 |
| 4,596,567 | 6/1986 | Iskra | 604/368 |
| 4,605,402 | 8/1986 | Iskra | 604/368 |
| 4,612,055 | 10/1971 | Mesek et al. | 604/365 |
| 4,842,927 | 6/1989 | Itoh et al. | 428/254 |

Primary Examiner—Stephen C. Pellegrino
Assistant Examiner—Gary Jackson
Attorney, Agent, or Firm—Dressler, Goldsmith, Shore, Sutker & Milnamow

[57] ABSTRACT

An absorbent panel structure, for use in a disposable diaper or the like, comprising at least about 400 percent by weight of superabsorbent material and at least one wicking layer of hydrophilic fiber particles. The absorbent panel has an average Taber stiffness value in the machine direction of less than about 7 and an absorptive capacity of at least about 300 ml.

20 Claims, 4 Drawing Sheets

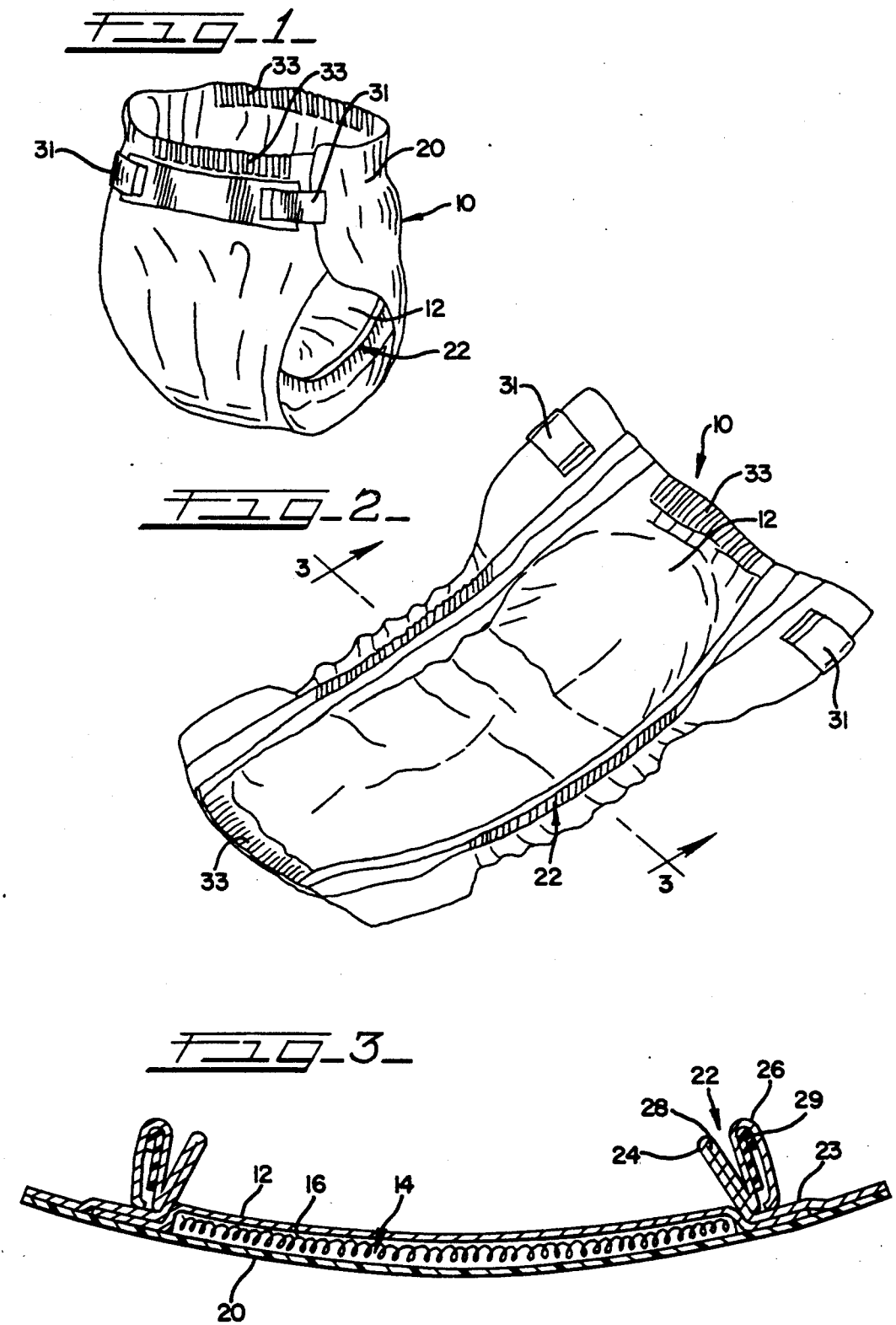

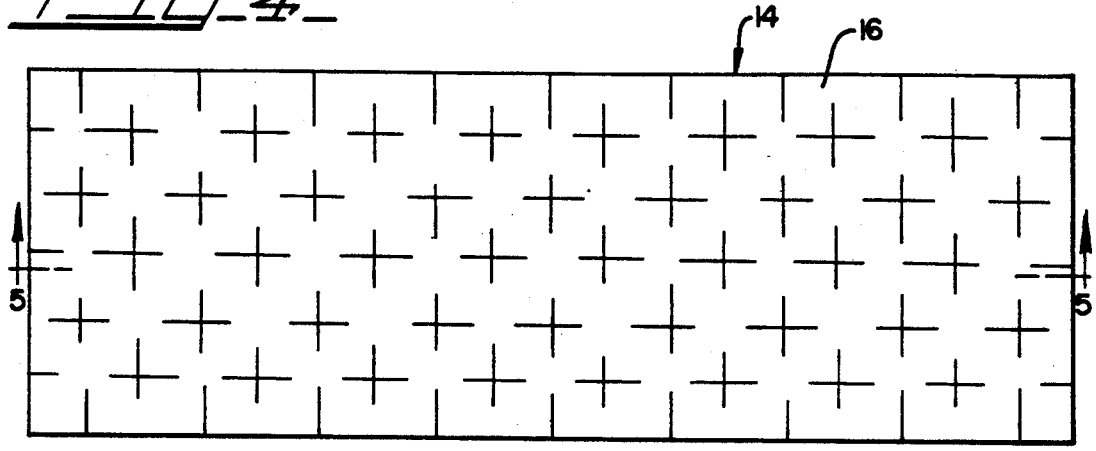
FIG-4-
FIG-5-
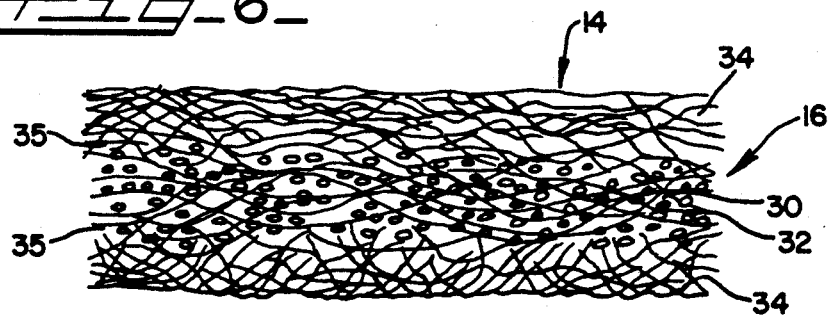
FIG-6-
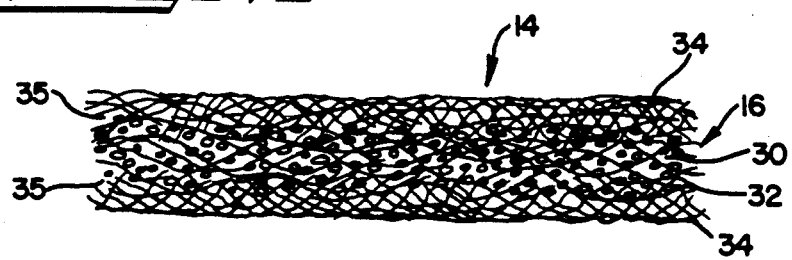
FIG-7-

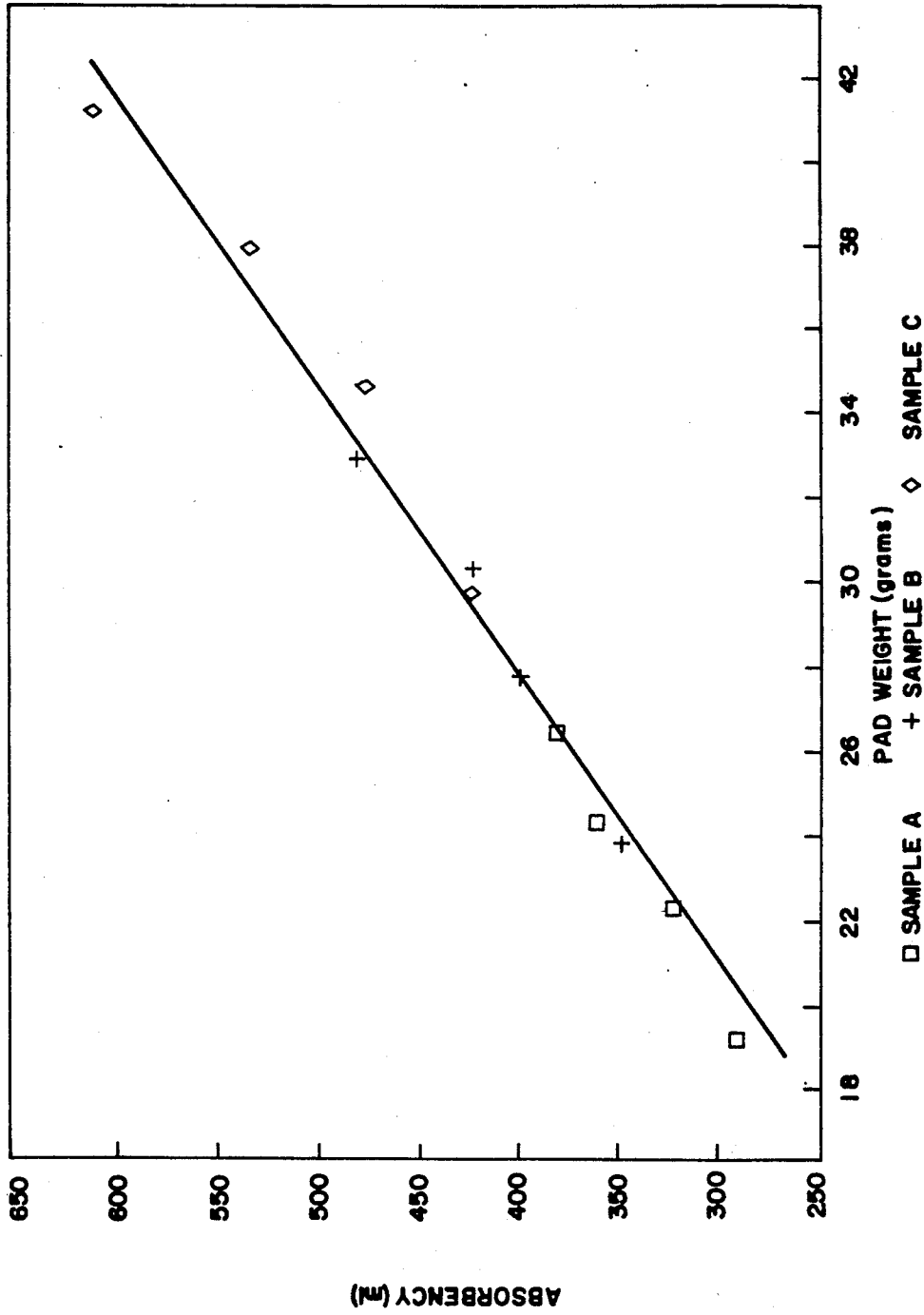

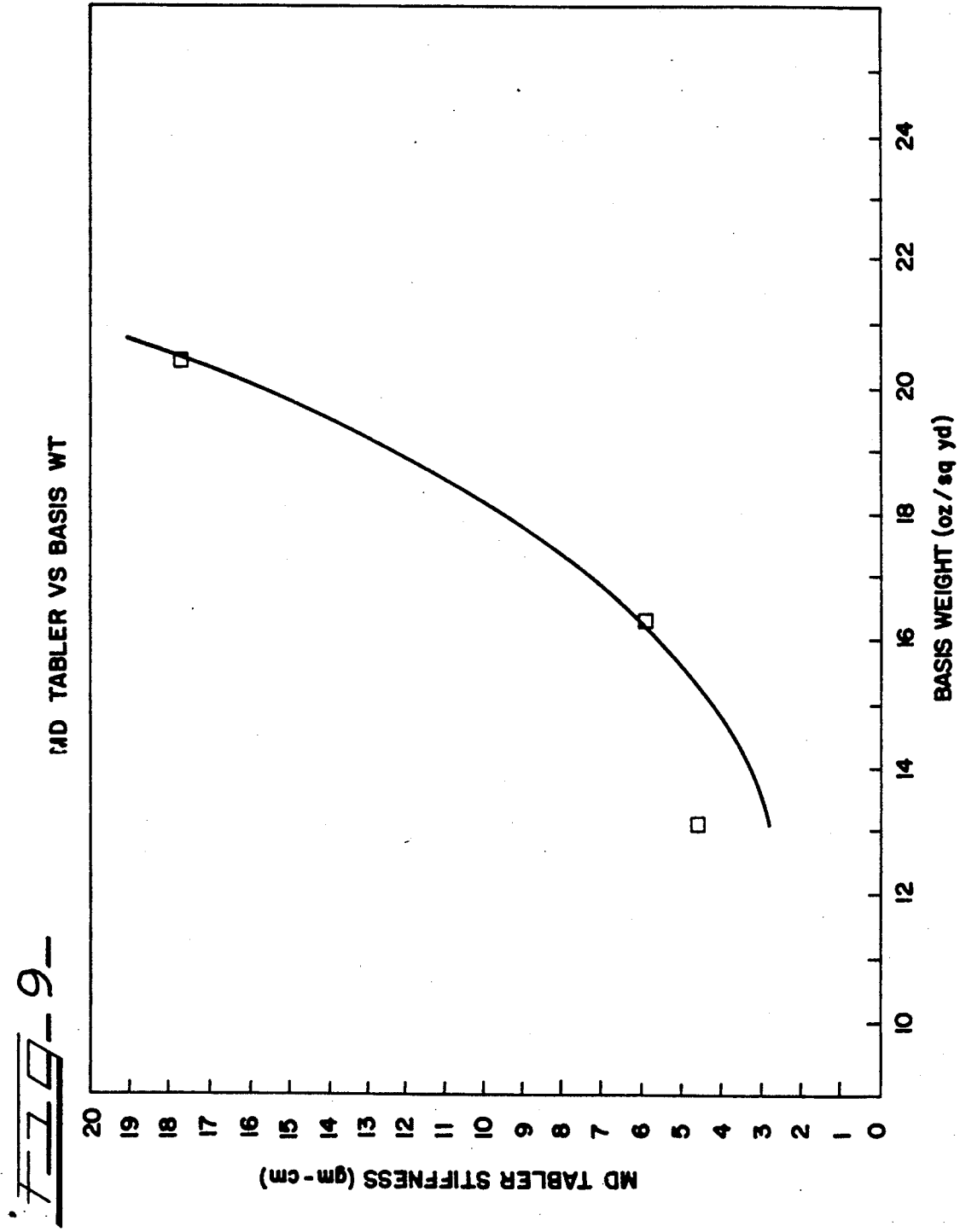

ABSORBENT PANEL STRUCTURE

FIELD OF THE INVENTION

The present invention relates to new and improved thin absorbent structures, and particularly, to new and improved absorbent structures containing superabsorbent material and which structures are thin and flexible and still absorb sufficient quantities of liquids. More specifically, the invention relates to such an absorbent structure for use in a disposable absorbent product such as a disposable diaper.

BACKGROUND OF THE INVENTION

Disposable absorbent products have been known for some time, including such products as disposable diapers, sanitary wound dressings, bandages, incontinent pads, and the like. These products incorporate an absorbent batt that is used to absorb and hold or contain body fluids. In years past, in many of these products, especially diapers and sanitary napkins, the absorbent batt comprised what is termed "wadding" or plies of tissue. The wadding was disposed between an impermeable backing sheet and a permeable facing sheet and the plies of tissue were used to absorb and contain the liquid within the product.

The wadding type of batt was replaced, for the most part, by an improved absorbent batt comprised of fluffed wood pulp fibers. This absorbent batt comprises a layer of individualized wood pulp fibers with the layer having substantial thickness. This diaper has improved absorbent capacity and somewhat better containment than a diaper using a wadding layer. Also the fluffed wood pulp layer is quite soft, flexible and conformable and hence, produces an improved diaper over diapers using wadding as the absorbent layer.

Though the fluffed wood pulp absorbent batts have improved capacity, the efficiency with which the capacity is used in a diaper or sanitary napkin is poor. The reason for this, is that the fluid to be absorbed is generally deposited in a localized area within the absorbent batt and the ability for the fluid to wick along the plane of the batt is poor. The fluid follows the path of least resistance and consequently moves to the closest edge of the batt where it generally is no longer contained and the product leaks. Furthermore, the wood pulp batts lack stability, e.g., when a diaper is being worn, the batt tends to sag and/or break up thereby creating bunching.

U.S. Pat. No. 3,017,304 discloses an absorbent product which incorporates in the batt a densified, paper-like layer. This paper-like layer acts as a wick, i.e., liquid which contacts the layer tends to move rapidly along the plane of the layer. When incorporated in combination with fluffed wood pulp fiber, the resultant product uses the absorbent capacity of the fluffed wood pulp much more efficiently. Diapers which incorporate this paper-like layer combined with fluffed wood pulp are disclosed and described in U.S. Pat. Nos. 3,612,055 and 3,938,522. Even though these products make much greater use of the capacity of the absorbent batt, they still do not totally contain the absorbed liquid.

A number of years ago "superabsorbent materials", i.e., materials which will absorb many times their weight of liquid, were developed. Since the development of such materials, various different approaches have been suggested to incorporate them in absorbent products such as diapers and sanitary napkins to enhance the absorptive performance of these products. Perhaps one of the first proposals to incorporate such a superabsorbent material in a disposable diaper is disclosed in U.S. Pat. No. 3,670,731. This patent discloses an absorbent dressing comprising an absorbent layer sandwiched between a permeable facing sheet and an impermeable backing sheet. The absorbent layer contains water insoluble cross-linked hydrocolloid polymer as the superabsorbent material.

In order for a superabsorbent material to function the liquid being absorbed must be transported to the superabsorbent material. In other words, the superabsorbent material must be placed in a position to be contacted by liquid discharged onto the absorbent body. Furthermore, as the superabsorbent material absorbs the liquid, it must be allowed to swell. If the superabsorbent is prevented from swelling, it will cease absorbing liquid. Hence, if the superabsorbent material is to function in diapers and sanitary napkins wherein the liquid to be absorbed is discharged in a small void area, the structure of the absorbent layer containing superabsorbent materials appears to be critical. Over the years a number of techniques have been disclosed in an attempt to provide structures which make efficient use of the superabsorbent material. Such products are typified by those in U.S. Pat. Nos. 4,103,062, 4,102,340, and 4,235,237. In addition, methods have been proposed for incorporating superabsorbents into suitable layers or suitable configurations which can be placed in an absorbent product, and examples of such proposals are disclosed in U.S. Pat. Nos. 4,186,165, 4,340,057, and 4,364,992.

In U.S. Pat. Nos. 4,500,315, 4,537,590, 4,540,454, 4,573,988, 4,596,567 and 4,605,402 particularly useful absorbent products are disclosed that include superabsorbent materials and utilize a substantial portion of such absorptive capacity of such superabsorbent materials. These products include a nonwoven fibrous web, such as polyester, which has associated with it at least 200 percent by weight, dry basis, of superabsorbent material to the dry basis weight of the web, to form an absorbing layer. In such products, in order to provide a product which will not only absorb liquid but also transport liquid, a wicking layer of wood pulp fibers or other suitable wicking materials are formed in a layer on at least one side of the absorbing layer. The product is then compressed to yield a relatively thin absorbing product with very substantial liquid absorbing capacity. However, the resulting compressed composite product is quite stiff, and hence it is preferred to soften the product to provide enhanced flexibility for utilization in products such as disposable diapers and the like. One method of reducing the stiffness of these products is to subject them to microcorrugating and then to perfembossing to reduce the stiffness in the manner as described in U.S. Pat. No. 4,605,402.

Fluff and wadding absorbent panels that have been used since the early 1970's were considered by those skilled in the art as being semi-rigid, at least when compared to more flexible portions of a diaper, such as a side flap. In U.S. Pat. No. 3,860,003 such known semi-rigid panels are characterized as a panel that has a Taber stiffness value of greater than 7. Efforts to develop suitable absorbent panels having a Taber stiffness value of less than 7 that function in disposable diaper constructions having side flaps have been attempted, but not met with success. Heretofore it was not thought possible to provide an absorbent panel that would provide adequate absorptive capacity, and yet have a Taber stiffness value less than about 7.

The present invention provides a new and improved absorbent structure that is thin and has a Taber stiffness value in the machine direction of less than about 7 and more preferably less than about 6. More specifically, the invention provides a new and improved superabsorbent containing absorbent panel structure for use in a disposable diaper, or the like, that is thin and has a Taber stiffness value less than about 6 and yet, surprisingly, has an absorptive capacity of at least about 300 ml and more preferably at least about 400 ml.

SUMMARY OF THE INVENTION

The absorbent panel structure in accordance with the present invention comprises an absorbent layer and a wicking layer. The absorbent layer comprises a fibrous web having superabsorbent material incorporated therein. The superabsorbent material is substantially uniformly disposed in among the fibers of the web in an amount of at least about 400 percent, by dry weight basis of the fibrous material in the web. The wicking layer is formed of suitable wicking materials such as wood pulp fibers and is placed on the fibrous web, and the two layers are compressed to yield a compressed composite structure. The fibrous web is maintained in a compressed state by the superabsorbent material, whereupon wetting and swelling of the superabsorbent material causes the fibrous web to expand from its compressed state due to the inherent resilience of the web. The compressed composite structure is microcorrugated and perf-embossed to yield a flexible structure having a low Taber stiffness value. The average Taber stiffness value in the machine direction or the absorbent structure is less than about 7, most preferably less than about 6, and it has an absorptive capacity of at least about 300 ml, most preferably at least about 400 ml. The average Taber stiffness value is obtained in accordance with the procedure described hereinbelow and is expressed herein as gram-centimeters.

In accordance with a preferred embodiment of the invention, the absorbent panel structure has a basis weight of from about 12.0 oz/yd$^2$ to about 17.0 oz/yd$^2$, most preferably about 16.4 oz/yd$^2$, and a panel weight of at least about 21 grams, most preferably about 32 grams. The absorbing layer preferably contains from about 400 percent to about 1200 percent by weight, dry basis, superabsorbent material to the dry basis weight of the web, most preferably about 750 percent, distributed therein. A wicking layer is preferably positioned substantially coextensive with at least a portion of each of the respective expansive surfaces of the absorbing layer and has a total basis weight of from about 5.0 oz/yd$^2$ to about 10.0 oz/yd$^2$, most preferably about 8.0 oz/yd$^2$ The absorbent panel structure preferably has a surface area from about 62 in$^2$ to about 92 in$^2$, most preferably about 85 in$^2$.

The disposable diaper embodying the absorbent panel structure of the invention includes a moisture-pervious facing layer or sheet positioned in overlying relationship on one side of the absorbent panel. The facing sheet is adapted for positioning adjacent the wearer of the diaper, and may typically comprise a non-woven fabric or the like. A backing layer or sheet is positioned on the side of the absorbent panel opposite the facing layer. The backing sheet may be formed from a moisture-impervious plastic sheet material. The resulting diaper is remarkably thin and flexible and, thereby, comfortable to the wearer, while still maintaining adequate absorptive capacity.

Other features and advantages of the present invention will become readily apparent from the following detailed description, the accompanying drawings, and the appended claims.

BRIEF DESCRIPTION OF THE DRAWINGS

FIG. 1 is a perspective view of a disposable diaper as completely assembled including an absorbent panel structure constructed in accordance with the principles of the present invention;

FIG. 2 is a perspective view of the diaper shown in FIG. 1 in the unfolded condition showing the top side thereof;

FIG. 3 is a cross-sectional view taken along lines 3—3 of FIG. 2;

FIG. 4 is a top plan view of the absorbent panel structure constructed in accordance with the principles of the present invention;

FIG. 5 is a cross-sectional view taken along lines 5—5 in FIG. 4;

FIG. 6 is an enlarged cross-sectional view of the absorbent panel structure prior to compression thereof;

FIG. 7 is an enlarged cross-sectional view of the absorbent panel structure after compression thereof;

FIG. 8 is a graph depicting test results of certain panel specimens showing the relationships between the absorbency and the panel weight; and FIG. 9 is a graph depicting test results of certain panel specimens showing the relationship between the Taber stiffness value and the basis weight of the panel.

DETAILED DESCRIPTION OF A PREFERRED EMBODIMENT

While the present invention is susceptible of embodiment in various forms, there is shown in the drawings and will hereinafter be described a presently preferred embodiment of the invention, with the understanding that the present disclosure is to be considered as an exemplification of the invention, and is not intended to limit the invention to the specific embodiment illustrated and described herein.

As used in the present disclosure, the term diaper is intended to refer to an absorbent article that is worn by an individual for absorbing and containing urine and/or fecal matter. It is to be understood that diapers embodying the principles of the present invention may be appropriately sized for use by infants or babies, and can further be sized for use by incontinent adults. It will be further understood that absorbent articles other than disposable diapers may be provided with an absorbent structure embodying the principles of the present invention. Such articles may include sanitary napkins, tampons, incontinent pads, wound dressing, absorbent wipes, and the like.

Referring now to the drawings, therein is illustrated in FIGS. 1-3 an exemplary disposable diaper 10 embodying an absorbent panel in accordance with the principles of the present invention. Diaper 10 includes a facing layer or top sheet 12 formed of moisture pervious material, with the facing layer being adapted for positioning adjacent to the wearer of the diaper. The diaper further includes an absorbent panel structure 14, which in the illustrated embodiment, is generally rectangular, but which may be otherwise shaped, such as hourglass-shaped, T-shaped, I-shaped, or otherwise contoured. As will be further described, absorbent panel structure 14 preferably comprises a compressed composite absorbent structure 16, containing an absorbent matrix of a resilient fibrous web with hydrocolloid or superabsorbent material distributed therein, with an associated wicking layer of densified cellulosic fibers provided on one or both of the expansive surfaces of the fibrous web for enhancing liquid transport within the absorbent matrix.

Disposable diaper 10 further includes a backing sheet 20 positioned on the side of the absorbent panel structure 14 which is opposite the facing layer 12. The backing sheet typically comprises a moisture-impervious material, such as plastic film or sheet. Diaper 10 may be provided with a double standing gather 22 consisting of an inner gather 24 and outer gather 26. Double standing gather 22 is preferably formed at the leg openings from a sheet of non-woven hydrophobic material 23 that is substantially impermeable to liquid while having vapor permeability characteristics, e.g. a fibrous non-woven fabric treated with silicone resin. Inner gather 24 is preferably elasticized by a monofilament rubber element 28 extending the length thereof and outer gather 26 is preferably elasticized by a folded polyurethane foam elastic material 29 extending the length thereof. Sheet 23 is preferably glued to backing sheet 20 by lines of hot melt adhesive As will be recognized by those familiar with the art, several different types of facing materials may be used for facing layer 12. For example, these layers may comprise a non-woven web made of a mixture of fibers consisting predominantly of inexpensive, short, cellulosic fibers, such as wood pulp fibers or cotton linters, with the remainder of the mixture being textile length fibers The non-woven webs may also be formed from polyester, polyethylene, polypropylene, nylon, rayon, or the like. The facing layer may be a laminate of one or more non-woven fabrics, each having differing physical properties.

In order to secure the diaper in position, adhesive tape fasteners 31, as are well known in the art, are provided on the rearward portions of the diaper. Each of these fasteners 31 include a tab-like element having pressure-sensitive adhesive thereon which, when brought into contact with a landing area associated with the forward, outer waist portion of the diaper, secures the diaper in position The diaper may also be provided with elasticized waistbands 33, as are well known in the art.

In order to improve the comfort of the diaper to the wearer, it is desirable to provide a diaper that is relatively thin and flexible and yet still possesses the necessary absorptive capacity. The present invention is particularly directed to an absorbent panel structure 14 for use in a diaper construction that possesses these characteristics. Although disclosed as a unitary structure, the absorbent panel may comprise coterminous or spaced panel strips. The absorbent panel may also be utilized in combination with another layer of absorbent material to form a laminate structure.

Referring to FIGS. 4–7, in accordance with a preferred embodiment, absorbent panel structure 14 comprises a compressed composite absorbent structure 16. The compressed composite absorbent structure 16 is preferably made substantially in the manner as disclosed in U.S. Pat. Nos. 4,500,315, 4,537,590, 4,540,454, 4,573,998, 4,596,567, and 4,605,402, the disclosure of which patents are incorporated herein by reference. Referring to FIG. 6, the compressed composite absorbent layer 16 comprises a substantially high loft, resilient fibrous web 30 with superabsorbent material 32 distributed within the fibrous web. The superabsorbent material is preferably in the form of a plurality of particles or globules of superabsorbent material disposed in a random and intermittent arrangement throughout the fibrous web. The particles or globules are of a size and spacing so that they do not interfere with the absorption of liquid by adjacent particles upon expansion of the resilient fibrous web 30.

The compressed composite structure 16 further includes liquid transport means in operative association with the absorbent fibrous web 30. The transport mechanism comprises at least one wicking layer 34 of densified hydrophilic fibers, with the wicking layer being coextensive with at least a portion of a respective expansive surface of the fibrous web layer of the absorbent matrix. Notably, this arrangement has been found to provide a very efficient absorbent structure, in that the densified wicking layer promotes liquid transport from a point of introduction to various portions of the associated fibrous web and superabsorbent. One of the problems typically encountered in employing superabsorbent materials in absorbent articles is the fact that such superabsorbents typically do not transport or wick liquid effectively, but rather can exhibit "gel blocking" upon wetting which can inhibit liquid transport through the material. Thus, the wicking layer of the compressed composite layer desirably promotes liquid transport for efficient utilization of the superabsorbent.

The fibrous web 30 is preferably formed from synthetic staple fibers, such as polyethylene, polypropylene, polyester, nylon, bicomponent fibers, and the like. Melt blown fibrous webs also are suitable. Generally, the fibers are air-laid or melt blown to form a web which, if needed, is then stabilized. Stabilization may be achieved by heat-through bonding, adhesive bonding, point embossing with heat or adhesive, and the like. The stabilization process is selected according to the fibers used and the process used to form the web. Suitable procedures for forming a web include carding, wet-laying, air-laying, or combinations of these, melt blowing and other suitable known techniques. The fibrous web preferably has a dry bulk of at least 20 cc/gm and a wet bulk of at least about 30 cc/gm. The fibrous web generally has a basis weight less than about 3 oz/yd$^2$, most preferably about 1.0 oz/yd$^2$.

The superabsorbent material 32 present in an intermittently dispersed form in the absorbing web 30 is generally a water-insoluble but water-swellable polymeric substance capable of absorbing water in an amount which is at least 10 times the weight of the substance in its dry form. The superabsorbent material is in the form of particles which may be in the shape of fibers, spheres, bits of film, globules, or the like, or may be applied in the form of a liquid monomer solution which is subsequently polymerized. Generally, the polymerized monomer solution provides globules and bits of film-like particles in the structure.

In one type of superabsorbent material, the particles or fibers may be described chemically as having a backbone of natural or synthetic polymers with hydrophilic groups or polymers containing hydrophilic groups being chemically bonded to the backbone or an intimate admixture therewith. Included in this class of materials are such modified natural and regenerated polymers as polysaccharides including, for example, cellulose and starch and regenerated cellulose which are modified being carboxyalkylated, phosphonoalkylated, sulphoalkylated or phosphorylated to render them highly hydrophilic. Such modified polymers may also be cross-linked to improve their water-insolubility.

These same polysaccharides may also serve, for example, as the backbone onto which other polymer moieties may be bonded by graft copolymerization techniques. Such grafted polysaccharides and their method of manufacture are described in U.S. Pat. No. 4,105,033 to Chatterjee et al. and may be described as polysaccharide chains having grafted thereon a hydrophilic chain. The preferred hydrophilic chains are hydrolyzed polyacrylonitrile chains and copolymers of polyacrylamide and polysodium arylate.

In addition to modified natural and regenerated polymers, the hydrocolloid particle component may comprise wholly synthetic hydrophilic particles. Examples of those now known in the art are polyacrylonitrile fibers which may be modified by grafting moieties thereon such as polyvinyl alcohol chains, polyvinyl alcohol itself, hydrophilic polyurethane, poly(alkyl phosphonates), partially hydrolyzed polyacrylamides (e.g., poly (N-N-dimethyl acrylamide), sulfonated polystyrene, or a class of poly(alkylene oxide). These highly hydrophilic synthetic polymers may be modified by other chemical treatments such as cross-linking or hydrolysis. Further examples known in the art are the non-ionic hydrophilic polymers such as polyoxyethylene, poloxypropylene and mixtures thereof which have been suitably cross-linked, either chemically or by irradiation. Still another more recent type is a derivative of isobutylene-maleic anhydride copolymer.

Hydrophilic polymers formed from water-soluble acrylate monomers, such as sodium, potassium, ammonium (or combination of cations), acrylate, may be placed on the absorbing layer by spraying or otherwise placing a solution thereon followed by polymerization and cross-linking, for example, by irradiation.

In addition, naturally occurring material such as gums, may be used. For instance, guar gum is suitable.

The superabsorbent material 32 is combined with the fibrous web 30 by means suitable to distribute the superabsorbent materials therein trying to minimize interference by one superabsorbent material with another upon the swelling of the first. If the superabsorbent material is a powder, it may be sprinkled onto the fibrous web either in dry form or the web may be moistened. If the superabsorbent is in granular form, it may be desirable to slightly moisten the superabsorbent before placing it in contact with the web. The superabsorbent material will contain particles which range in size from about 0.005 mm in diameter to globules that are continuous along fibers for a distance up to several inches.

Another method of placing the superabsorbent material in the web is spraying a monomer solution on the web or saturating the web with a monomer solution followed by polymerization of the monomer. One typical way to polymerize the monomer is by use of irradiation. It is desirable to place the superabsorbent somewhat evenly throughout the fibrous web. However, even if the superabsorbent is powderlike and in the form of a layer, it tends to function better than such a layer has in previously known products. It may be desirable to place more superabsorbent in one area than in another and/or to place the superabsorbent in the structure in predetermined patterns. Any superabsorbent which absorbs large amounts of liquids is suitable for use in the absorbing layer of the present invention.

In accordance with a most preferred embodiment of the invention, droplets of the superabsorbent material are dispersed within the web by moving the web through a droplet-flicking zone and flicking droplets of the superabsorbent material, in a liquid carrier, onto opposite sides of the web as the web is moved through the droplet-flicking zone. On each of opposite sides of the fibrous web, a rotating brush has bristles, picking up the material, in the liquid carrier, and flicking droplets thereof as the brush rotates. The superabsorbent material is polymerized and cross-linked in situ. This method is fully disclosed in U.S. patent application Ser. No. 335,764, filed on Apr. 10, 1989, which application is assigned to the same assignee as the present invention. The disclosure in such application is incorporated herein by reference.

The wicking layer(s) 34 is comprised of hydrophilic fibers, such as rayon fibers, cellulosic fibers, peat moss, acrylic fibers, or mixtures thereof. The cellulosic fibers include wood pulp fibers, cotton linters, and the like. The wood pulp fibers generally are those that are used to form the fluff or fibrous batt layer in conventional absorbent products such as disposable diapers, sanitary napkins, etc. Other cellulosic fibers that might be used are rayon fibers, flax, hemp, jute, ramie, cotton and the like. The fibers or peat moss or mixtures thereof are placed in such a way as to form a layer in which the particles are close to one another so as to provide a higher capillary pressure to promote wicking of liquid in the plane of the layer. What appears to be only a small difference in capillary pressure is all that is required for one layer to attract and drain liquid from an adjacent layer.

The wicking layer 34 can be preformed and placed next to the absorbing layer 30 before compression or the wicking layer particles can be air-laid, mechanically entangled therewith, or wet-laid on to the absorbing layer before compression.

A transition zone 35 is formed at the junction of the absorbing layer 30 and the wicking layer 34. Some of the particles, e.g., fibers, of the wicking layer extend into and become integral with the absorbing layer. The region in which the majority of the extending particles lie is identified as the transition zone. In the transition zone, there is a composite of absorbing layer fibers, superabsorbent material, and wicking layer particles. The wicking layer particles which extend into the absorbing layer are in intimate contact with some of the superabsorbent material of the absorbing layer. This permits the liquid to commence its migration in the z direction to reach the superabsorbent material. As the liquid progresses in the z direction, the superabsorbent material becomes soft and releases the absorbing layer fibers which permit the absorbing layer to return substantially to its uncompressed thickness or more, i.e., from the thickness shown in FIG. 7 to the thickness shown in FIG. 6. As the absorbing layer returns to its uncompressed thickness, larger void areas are provided for storage of the liquid and for increased swelling of the superabsorbent material as it absorbs the liquid residing in the void areas. The absorbing layer tends to return to its uncompressed thickness or more, probably because of both the resiliency of the fibers and the swelling of the superabsorbent material.

In order for the absorbing layer fibrous web to provide the necessary medium for absorbing liquid, it is preferred that the fibrous web has an initial dry bulk of at least about 20 cc/gm, a dry bulk recovery of at least 30 percent, (preferably 50 percent), a wet bulk of at least about 30 cc/gm, and a basis weight of less than about 3 oz/yd² The initial dry bulk is the area times thickness of the layer under a load of 0.01 pounds per square inch calculated in cubic centimeters. This value is divided by the weight in grams in order to provide the measurement in cubic centimeters per gram. The dry bulk recovery is obtained by subjecting the web to a load of 1.75 psi for five minutes, removing the load and allowing the web to rest for one minute, subjecting the web to a load of 0.01 psi for one minute and then measuring the final dry bulk while under the 0.01 psi load. The dry bulk recovery is the final bulk divided by the initial bulk expressed in percent. The wet bulk is measured in the same manner as the initial dry bulk except that the web has been saturated with water. If the fibrous web is provided with a dry bulk recovery of at least 20 percent (preferably 50 percent), an initial dry bulk of at least 40 cc/gm. a wet bulk of at least 30 cc/gm, with a web basis weight of less than 3.0 oz/yd², the fibrous web can retain superabsorbent material up to at least 1,200 percent of the dry basis weight of the web. It is preferably that the web contain 400 percent to 1,500 percent by weight, dry basis, superabsorbent to the dry basis weight of the web and most preferred is a range from about 600 percent to about 1,000 percent.

The resulting compressed composite structure is too stiff for most uses due to the high loading of superabsorbent particles in the absorbing layer. The structure is softened to a low Taber stiffness value by subjecting it to mechanical working procedures. In accordance with a preferred embodiment such mechanical working procedures include a microcorrugating procedure and then a perf-embossing procedure substantially in the manner as disclosed in U.S. Pat. No. 4,605,402, the disclosure of which patent is incorporated herein by reference. The compressed composite structure is reduced to a moisture content less than 10%, preferably less than about 6%, most preferably about 5%, and directed through microcorrugating rolls preferably in the machine direction. The microcorrugating rolls are preferably set with an interference of 0.025 to 0.03 inch in the machine direction and about 0.01 inch in the cross direction in order to break up the superabsorbent particles to a somewhat uniform size and create hinge lines resulting in a flexible, pliable, soft feel. The microcorrugated compressed composite structure is then subjected to perfembossing wherein the superabsorbent particle size is further reduced. During the perf-embossing procedure, the compressed composite is passed through a pair of rolls which have knuckles and which intermesh to shear the structure to produce raised areas produced by lower knuckles and depressed densified areas produced by upper knuckles. Interconnecting the raised areas and the depressed areas are intermediate portions which have received most of the mechanical working. At locations where the upper knuckles pass very close to the lower knuckles of the rolls, the work applied to the composite structure produces apertures in it. The length of the apertures can be varied by controlling the overlap of the upper knuckles and lower knuckles or the size of the knuckles of the rolls. The preferred structure of the present invention employs controlled portions of both apertures and partially fractured or sheared regions by setting the engagement of the rolls at about 0.015 inch.

It has been discovered that the absorptive capacity of a compressed composite absorbent panel structure is dependent upon the weight of the panel and that the Taber stiffness value of the panel is dependent upon the basis weight of the panel. That is, as the weight of the panel is increased, the absorptive capacity of the panel increases and as the basis weight of the panel decreases, the Taber stiffness value of the panel decreases. Accordingly, efforts to decrease the Taber stiffness value of the panel by reducing the basis weight of the panel also tends to decrease the absorptive capacity of the panel. Likewise, efforts to increase the absorptive capacity of the panel by increasing the weight of the panel tends to increase the Taber stiffness value of the panel.

It has been discovered that a compressed composite absorbent panel having a low Taber stiffness value of less than about 7 and an adequate absorptive capacity in excess of about 300 ml can be achieved by the strategic selection of the basis weight of the panel and the weight of the panel. It has also been discovered that such a panel having a basis weight less than about 17.0 oz/yd² has a Taber stiffness value less than about 7. A panel having a basis weight less than about 16.4 oz/yd² has a Taber stiffness value less than about 6. It has further been discovered that a compressed composite absorbent panel having a panel weight of at least about 21 grams has an absorptive capacity of at least about 300 ml. It has also been discovered that such a panel having a panel weight of at least about 28 grams has an absorptive capacity of at least about 400 ml.

In accordance with the principles of the invention, the absorbent compressed composite panel structure 16 has a Taber stiffness value in the machine direction of less than about 7, most preferably less than about 6, and an absorptive capacity of at least about 300 ml, most preferably at least about 400 ml. As used herein the absorptive capacity and the Taber stiffness value are determined in the manner as disclosed in the description of the Examples that hereinbelow follows. The basis weight of the absorbent panel is preferably from about 12.2 oz/yd² to about 17.0 oz/yd². The weight of the absorbent panel is preferably from about 21 grams to about 40 grams, most preferably from about 28 grams to about 38 grams.

The absorbing layer 30 of the absorbent panel 16 contains from about 400 percent to about 1200 percent by weight, dry basis, of the fibers, most preferably from about 600 percent to about 1000 percent, of superabsorbent material 32 dispersed therein. The basis weight of the fibers in the absorbing layer 30 is less than about 3.0 oz/yd², most preferably about 1.0 oz/yd². A wicking layer 34 is preferably positioned on each side of the absorbing layer 30. The total basis weight of the wicking layer or layers is preferably from about 5.0 oz/yd² to about 10.0 oz/yd², most preferably about 8.0 oz/yd². The layers 34 may be of equal or unequal basis weight. However, it has been determined that the Taber stiffness value is lower when the basis weights of the layers 34 are substantially the same.

As will be apparent to one skilled in the art, the area of the absorbent panel made from a particular basis weight compressed composite material determines the weight of the panel. Accordingly, it is necessary to select an appropriate area for the absorbent panel dependent upon the basis weight of the compressed composite material to be utilized and the desired weight of the panel necessary to achieve a particular absorptive capacity. The area of the absorbent panel is preferably from about 62 in² to about 92 in², most preferably about 85 in².

The absorbent panel structures of the present invention are further disclosed in the discussion of the following examples and the discussion of certain test procedures that are utilized to determine the absorptive capacity and the Taber stiffness value of the exemplary panels.

EXAMPLES

Absorbent panel structures are made from sheets of compressed composite material having three different basis weights (Samples A, B and C) that are constructed in the manner as discussed hereinabove. The compressed composite sheets have an absorbing layer made from a low density non-woven fibrous web containing polyester fibers (DuPont D280W fiber) and conjugate fibers (BASF Bico 1060 fiber), with about 80% of the fibers by weight being polyester fibers. The fibrous web has applied to it polymerized potassium acrylate superabsorbent material in the manner as described in above mentioned U.S. Pat. application Ser. No. 335,764. A wicking layer of pulp fibers (Weyerhaeuser NB 316) is applied to both sides of the absorbing layer. The composite structure is compressed and softened by microcorrugating and perfembossing as described in U.S. Pat. No. 4,605,402. The basis weights of the compressed composite Samples A, B and C are set for in Table I as follows:

TABLE I

| | Basis Weights | | |
|---|---|---|---|
| | Sample A | Sample B | Sample C |
| Total Basis Wt. (oz/yd$^2$) | 13.14 | 16.35 | 20.52 |
| Fibrous Web Basis Wt. (oz/yd$^2$) | 0.89 | 1.05 | 1.33 |
| Polymer Basis Wt. (oz/yd$^2$) | 6.17 | 7.40 | 9.98 |
| Pulp Basis Wt. (oz/yd$^2$) side 1 | 1.46 | 3.95 | 4.61 |
| Pulp Basis Wt. (oz/yd$^2$) side 2 | 4.62 | 3.96 | 4.60 |

Absorbent panels of each of four different sizes are made from compressed composite Samples A, B and C. The sample sizes are 4.50 inches wide and 14.75 inches long, 5.25 inches wide and 14.75 inches long, 5.75 inches wide and 14.75 inches long, and 6.25 inches wide and 14.75 inches long. The total panel weights of the absorbent panels are set forth in Table II as follows.

TABLE II

| | Panel Weight (gm) | | | |
|---|---|---|---|---|
| | Panel Width (in) | | | |
| | 4.50 | 5.25 | 5.75 | 6.25 |
| Sample A | 19.3 | 22.2 | 24.5 | 26.5 |
| Sample B | 23.6 | 27.5 | 30.2 | 33.0 |
| Sample C | 29.7 | 34.4 | 37.8 | 42.2 |

Each of the compressed composite Samples A, B and C is tested to determine its Taber stiffness value and each of the absorbent panels is tested to determine its absorptive capacity in accordance with the test procedures described immediately hereinbelow.

The Taber stiffness of each of the compressed composite Samples A, B and C is determined in accordance with the procedure generally set forth in accordance with TAPPI standard T489 05-70. A Taber V-5 instrument Model 150-D, 0–100 gram-centimeter range, stiffness tester is used to measure the flexural rigidity of each of the compressed composite samples. The samples are tested in both the machine direction (MD) and cross direction (CD). Ten test specimens of 2.75 inches by 1.5 inches are cut by a suitable die from each of the Samples A, B and C, with five of the test specimens having the 2.75 inches dimension in the machine direction and five of the test specimens having the 2.75 inches dimension in the cross direction. The specimens are maintained in conditions of 73±2° F. and humidity of 50±2% for 16 hours. The "Driving Disc" of the instrument is set to zero on the scale and the instrument is appropriately leveled. One end of the specimen is clamped into the upper clamp and is centered in the clamp with the direction of the specimen to be read (either MD or CD) in a vertical position. The operating switch is actuated and the "R" and "L" Taber stiffness units are read and recorded. The above procedure is repeated on a total of six specimens for each of the compressed composite samples with the machine direction at the 2.75 inches length. The procedure is repeated on a second set of six specimens for each of the compressed composite samples with the cross direction at the 2.75 inches length. The recorded "R" and "L" Taber stiffness units are averaged together for the six specimens to determine the Taber stiffness value in gram-centimeters of each compressed composite sample.

The Taber stiffness value for Samples A, B and C is set forth in Table III as follows:

TABLE III

| | Taber Stiffness | |
|---|---|---|
| | MD | CD |
| Sample A | 4.6 | 3.0 |
| Sample B | 5.9 | 4.3 |
| Sample C | 17.7 | 8.7 |

The absorptive capacity of each of the absorbent panels is determined in accordance with the following test procedure. The absorbent panel is dried at 200° F. for 2 hours. The dry panel is weighed and the weight is recorded. The dry panel is enclosed in an envelope made of polypropylene backing material with the edges sonically sealed. The outside dimensions of the envelope are 3 inches greater than the length and width dimensions of the panel and the seals are made ⅛ inch from the envelope edges in a manner which permits liquid to permeate the envelope and contact the panel. A control envelope without a panel is made of equal size. The panel envelope and the control envelope are immersed into a container of 1% saline solution and are left in a flat position for one hour. The envelopes are then removed from the container and suspended in a vertical position and permitted to drip for 10 minutes. The envelopes are weighed and the weight recorded. The absorptive capacity of the absorbent panel is calculated by subtracting the weight of the dry panel and the weight of the immersed control envelope from the weight of the immersed panel envelope. Three specimens of each of the absorbent panels are tested in accordance with the above procedure and an average absorptive capacity is calculated.

The absorptive capacity of each of the absorbent panels is set forth in Table IV as follows:

TABLE IV

| | Absorptive Capacity (ml) | | | |
|---|---|---|---|---|
| | Panel Width (in) | | | |
| | 4.50 | 5.25 | 5.75 | 6.25 |
| Sample A | 291 | 323 | 361 | 381 |

TABLE IV-continued

| | Absorptive Capacity (ml) Panel Width (in) | | | |
|---|---|---|---|---|
| | 4.50 | 5.25 | 5.75 | 6.25 |
| Sample B | 349 | 400 | 424 | 482 |
| Sample C | 425 | 478 | 536 | 614 |

Referring to FIG. 8, a graph is presented plotting the absorptive capacity of each of the absorbent panel test specimens from Table IV against the panel weight of each of the specimens from Table II. From this graphical representation it has been determined that there is generally a linear relationship between the absorptive capacity of a compressed composite panel and the weight of the panel. Referring to FIG. 9, a graph is presented plotting the Taber stiffness value of each of the compressed composite Samples A, B and C from Table III against the basis weight of each of the samples from Table I. It should be observed that the basis weights of the wicking layers 34 are substantially the same in Samples B and C and are approximately a 72/25 relationship in Sample A. As noted above, it has been determined that the Taber stiffness value of the panel is reduced when the basis weights of the wicking layers are substantially the same. The graph as presented in FIG. 9 has been prepared to approximate a reduced Taber stiffness value for Sample A as if such Sample had been made with wicking layers of substantially equal basis weights.

From the foregoing it will be observed that numerous variations and modifications may be effected without departing from the true spirit and scope of the novel concepts of this invention.

What is claimed is:

1. An absorbent panel structure, comprising:
   an absorbing layer comprised of a substantially high loft, inherently resilient fibrous web containing at least about 400 percent dry basis weight of superabsorbent material to the dry basis weight of the fibers distributed therein, said fibrous web being maintained in a compressed state by said superabsorbent material such that upon wetting of said superabsorbent material said fibrous web expands from its compressed state due to the inherent resilience of said fibrous web to facilitate swelling of said superabsorbent material;
   at least one wicking layer of densified hydrophilic fiber particles, said at least one wicking layer being coextensive with at least a portion of a respective expansive surface of said fibrous web to promote liquid transport within said absorbing layer; and
   said absorbent panel having an average Taber stiffness value in the machine direction of less than about 7, a panel weight of at least about 21 grams, and an absorptive capacity of at least about 300 ml.

2. The absorbent panel structure as defined in claim 1 wherein said absorbent panel has a basis weight less than about 17.0 oz/yd$^2$.

3. The absorbent panel structure as defined in claim 1 wherein said absorbent panel has a basis weight from about 12.0 oz/yd$^2$ to about 17.0 oz/yd$^2$.

4. The absorbent panel structure as defined in claim 1 wherein the dry basis weight of the superabsorbent material distributed in said absorbing layer is from about 600 percent to about 1000 percent of the dry basis weight of said fibrous web.

5. The absorbent panel structure as defined in claim 1 has a surface area from about 62 in$^2$ to about 92 in$^2$.

6. The absorbent panel structure as defined in claim 1 wherein said at least one wicking layer has a basis weight from about 5.0 oz/yd$^2$ to about 10.0 oz/yd$^2$.

7. The absorbent panel structure as defined in claim 1 wherein said absorbent panel structure is microcorrugated.

8. The absorbent panel structure as defined in claim 7 wherein said absorbent panel structure has a moisture content as made of less than about 6.0 percent.

9. The absorbent panel structure as defined in claim 1 wherein said absorbent panel structure is perfembossed.

10. The absorbent panel structure as defined in claim 1 has a panel weight from about 21 grams to about 40 grams.

11. The absorbent panel structure as defined in claim 10 has a basis weight from about 14.0 oz/yd$^2$ to about 17.0 oz/yd$^2$.

12. The absorbent panel structure as defined in claim 1 has a panel weight from about 28 grams to about 38 grams.

13. A disposable diaper including an absorbent panel positioned between a substantially liquid impervious backing sheet and a relatively liquid pervious facing sheet, said absorbent panel comprising:
   an absorbing layer comprised of a substantially high loft, inherently resilient fibrous web containing about 400 percent to about 1200 percent dry basis weight of superabsorbent material to the dry basis weight of the fibers distributed therein, said fibrous web being maintained in a compressed state by said superabsorbent material such that upon wetting of said superabsorbent material said fibrous web expands from its compressed state due to the inherent resilience of said fibrous web to facilitate swelling of said superabsorbent material;
   at least one wicking layer of densified hydrophilic fiber particles, said at least one wicking layer being coextensive with at least a portion of a respective expansive surface of said fibrous web to promote liquid transport within said absorbing layer;
   said absorbent panel having a basis weight from about 12.0 oz/yd$^2$ to about 17.0 oz/yd$^2$, a panel weight of at least about 21 grams, an average Taber stiffness value in the machine direction of less than about 7 and an absorptive capacity of at least about 300 ml.

14. The disposable diaper as defined in claim 13 wherein the dry basis weight of the superabsorbent material distributed in said absorbing layer is rom about 600 percent to about 1000 percent of the dry basis weight of said fibrous web.

15. The disposable diaper as defined in claim 14 wherein said absorbent panel has a surface area from about 62 in$^2$ to about 92 in$^2$.

16. The disposable diaper as defined in claim 15 wherein said absorbent panel is microcorrugated and perf-embossed.

17. The disposable diaper as defined in claim 15 wherein said at least one wicking layer includes a wicking layer positioned substantially coextensive with at least a portion of each of the respective expansive surfaces of said absorbing layer.

18. The disposable diaper as defined in claim 17 wherein said wicking layers have a combined basis weight of about 8.0 oz/yd$^2$.

19. The disposable diaper as defined in claim 17 wherein the basis weight of each of the wicking layers is substantially the same.

20. The disposable diaper as defined in claim 13 herein said absorbent panel has a weight from about 28 grams to about 38 grams.

* * * * *